United States Patent [19]

Essex et al.

[11] Patent Number: 5,731,142
[45] Date of Patent: Mar. 24, 1998

[54] ASSAY FOR DETECTING INFECTION BY HTLV-III

[75] Inventors: Myron E. Essex, Sharon; Tun-Hou Lee, Newton, both of Mass.

[73] Assignee: President and Fellows of Harvard College, Cambridge, Mass.

[21] Appl. No.: 245,077

[22] Filed: May 17, 1994

Related U.S. Application Data

[63] Continuation of Ser. No. 539,370, Jun. 18, 1990, abandoned, which is a continuation of Ser. No. 56,134, May 29, 1987, abandoned, which is a division of Ser. No. 670,361, Nov. 9, 1984, Pat. No. 4,725,669.

[51] Int. Cl.$^6$ .................. C12Q 1/70; G01N 33/564; C07K 14/16
[52] U.S. Cl. .............. 435/5; 435/810; 435/974; 530/395; 530/826
[58] Field of Search .............. 435/5, 974, 810; 530/395, 826

[56] References Cited

U.S. PATENT DOCUMENTS

| | | | |
|---|---|---|---|
| 4,520,113 | 5/1985 | Gallo | 436/504 |
| 4,524,027 | 6/1985 | Bohn | 436/543 |
| 4,708,818 | 11/1987 | Montagnier et al. | 435/5 |
| 4,716,102 | 12/1987 | Levy | 435/5 |

FOREIGN PATENT DOCUMENTS

| | | | |
|---|---|---|---|
| 0 201 588 | 1/1995 | European Pat. Off. | |
| WO 85/04903 | 11/1985 | WIPO | |
| WO 86/02383 | 4/1986 | WIPO | C12P 21/00 |

OTHER PUBLICATIONS

Veronese et al., Science 229:1402–1405, 1985.
Popovic et al., Science 224:497–500, 1984.
Montagnier et al., Science 225:63–66, 1984.
Kalyanaraman et al., Science 225:321–323, 1984.
Gallo et al., Science 224:500–503, 1984.
AKZO Opposition to EP 0 201 588 and attachments (103 pages).
Eisenberg et al., Effect of Monoclonal Antibodies on Limited Proteolysis of Native Glycoprotein gD of Herpes Simplex Virus Type 1, J. Virology 41:478–488, 1982.
Matthews et al., Synthesis and Processing of Glycoprotein D of Herpes Simplex Virus Type 1 and 2 in an Vitro System, J. Virology 48:521–533, 1983.
Synder et al., The Feline Oncornavirus–Associated Cell Membrane Antigen (FOCMA) Is Related to, but Distinguishable from, FeLV–C gp70, Virology 131:315–327, 1983.
Fletcher et al., Chromatographic Separation and Antigenic Analysis of Proteins of the Oncornaviruses Virology 64:358–366, 1975.
Tung et al., Relationships of gp70 of MyLV Envelopes to gp70 Components of Mouse Lymphocyte Plasma Membranes J. Exp. Med. 146:1280–1284, 1977.
Potocnjak et al., Science 215:1637–1639 (1982).
Sangaharan et al., Science 224:168–174 (1984).

Muesing et al., Nature 313:450–458 (1985).
Allan et al., Science 288:1091–1094 (1985).
Kitchen et al., Nature 312:367–369 (1984).
Cleveland et al., J. Biol. Chem. 252:1102–1106 (1977).
Snyder et al., Cold Spring Harbor Symposia on Quntitative Biology, vol. ILIV, pp. 787–799 (1980).
Morgan et al., J. Virology 46:177–186 (1983).
Robey et al., Proc. Nat'l Acad. Sci. (USA) 83:7023–7027 (1986).
Barin et al., Science 228:1094–1096 (1985).
Sangaharan et al., Science 224:506–508 (1984).
Schupbach et al., "Serological Analysis of a Subgroup of Human T–Retroviruses (HTLV–III) Associated with AIDS" Science 224:503–506 (1984).
Hahn et al., "Molecular cloning and characterization of the HTLV–III virus associated with with AIDS" Nature 312:166–169 (1984).
Ho et al., "HTLV–III in the Semen and Blood of a Healthy Homosexual Man" Science 226:451–453 (1984).
Safai et al., "Seroepidemiological Studies of Human T–Lymphotrophic Retrovirus Type III in Acquired Immunodeficiency Syndrome" Lancet, Jun. 30, 1984, 1438–1440.
Pan et al., J. Infect. Dis. 135:626–631 (1987).
Towbin et al., Proc. Nat'l Acad. Sci. USA 76:4350–4354 (1979).
Erickson et al., J. Immunol. Methods 51:241–249 (1982).
Chang–Meyer et al., Virol. 181:288–294 (1991).
McClure et al., Current Topics in AIDS, vol. 1, Ch. 5, pp. 95, 102–105.
Mortimer et al., Current Topics in AIDS, vol. 1, Ch. 7, pp. 133, 140–141, 150–151.
Eisenberg et al., J. Virol. 41:478–488 (1982).
Matthews et al., J. Virol. 48:521–523 (1983).
Snyder et al., Virology 131:315–327 (1983).
Fletcher et al., Virology 64:358–366 (1975).
Tung et al., J. Exp. Med. pp. 1280–1284 (1978).
Sodroski et al., Science 22:421–424 (1984).
Lee et al., Proc. Natl. Acad. Sci. USA 81:3856–3860 (1984).

(List continued on next page.)

*Primary Examiner*—Michael P. Woodward
*Attorney, Agent, or Firm*—Fish & Richardson P.C.

[57] ABSTRACT

A first glycoprotein having a molecular weight of approximately 120,000 daltons in the H9/HTLV–III cell line, of which approximately 90,000 daltons is the unglycosylated moiety, is obtained from cells infected with human T-cell leukemia virus, type III. A second glycoprotein having a molecular weight of approximately 160,000 daltons is also obtained from such cells, of which approximately 90,000 daltons is the unglycosylated moiety and is substantially identical to the unglycosylated moiety of the first glycoprotein.

The presence, in a biological specimen, of either of these unglycosylated or of the unglycosylated moiety is indicative of the presence of cells infected by human T-cell leukemia virus. An assay for the glycoprotein or its unglycosylated moiety is a useful diagnostic procedure for determining such infection in biological specimens.

10 Claims, 2 Drawing Sheets

OTHER PUBLICATIONS

Robey et al., Proc. Nat'l. Acad. Sci. (USA) (1986) 83:7023–7027.

Barin et al., Science (1985) 228:1094–1096.

Sarngadharan et al., Science (1984) 224:506–508.

Pan et al., J. Infect. Dis. (1987) 135:626–631.

Towbin et al., Proc. Nat'l. Acad. Sci. USA (1979) 76:4350–4354.

Erickson et al., J. Immunol. Methods (1982) 51:241–249.

Schupbach et al, "Serological Analysis of a Subgroup of Human T–Retroviruses (HTLV–III) Associated with AIDS" Science, 224(1984) 503–506.

Hahn et al, "Molecular cloning and characterization of the HTLV–III Virus associated with AIDS" Nature, 312(1984) 166–169.

Ho et al. "HTLV–III in the Seman and Blood of a Healthy Homosexual Man" Science, 226 (1984) 451–453.

Safai et al, "Seroepidemiological Studies of Human T–Lymphotropic Retrovirus type III in Acquired Immunodeficiency Syndrome" Lancet, Jun. 30, 1984 1438–1440.

Kitchen et al, "Aetiology of AIDS–antibodies to human T–Cell Leukaemia Virus (type III) in haemophiliacs" Nature 312(1984)367–9.

ASSAY FOR DETECTING INFECTION BY HTLV-III

This is a continuation of application Ser. No. 07/539,370, filed on Jun. 18, 1990, which is a continuation of application Ser. No. 07/056,134, filed May 29, 1987, each of which is now abandoned, and which is a divisional of application Ser. No. 06/670,361, filed Nov. 9, 1984, issued U.S. Pat. No. 4,725,669.

This invention was made with Government support, and the Government has certain rights in the invention.

BACKGROUND OF THE INVENTION

This invention relates to novel purified forms of glycoprotein found in the cell surface membrane of cells infected with human T-cell leukemia virus, type III (HTLV-III), and to an assay for detecting in a biological specimen the presence of an antibody to the antigenic determinants present in said glycoproteins.

HTLV-III is suspected of playing a key role in the pathogenesis of the acquired immunodeficiency syndrome (AIDS). It has been shown that human patients whose bodies contain antibodies to HTLV-III-infected cells are apparently latently or actively infected with the virus.

SUMMARY OF THE INVENTION

It has now been found that particular polypeptides or glycoproteins present on the cell surface of human cells infected with HTLV-III, when purified and isolated, contain an antigenic determinant or determinants which provide a high degree of sensitivity and immunospecificity for antibody to human cells infected with HTLV-III. Consequently, the substantially pure glycoproteins or their unglycosylated moieties are useful as a diagnostic tool for assaying biological specimens to determine whether they contain cells which have been infected by HTLV-III. Other polypeptides containing immunologically cross-reactive antigenic determinants are useful for the same purpose. By "polypeptides containing immunologically cross-reactive antigenic determinants" is meant polypeptides having in common antigenic determinants with which a given antibody will react. Such other polypeptides include the unglycosylated moieties of the glycoproteins. Other useful polypeptides or proteins, which have the necessary immunogenic determinants, include synthetic polypeptides. They also include antibodies or fragments thereof which are anti-idiotypic towards the active determinant or determinants on the glycoprotein of the invention. It has also been shown that anti-idiotypic reagents are useful as diagnostic tools for the detection of antigens carrying sites which are immunologically cross-reactive with those on the antibodies (Potocnjak et al., Science 215: 1637–1639 (1982) herein incorporated by reference). Thus, an assay for HTLV-III infected cells could be carried out with the aid of an anti-idiotypic antibody or immunologically active fragment thereof which carries an antigenic site or sites thereon which are immunologically similar to the antigenic site or sites on the glycoprotein of the invention. Such anti-idiotypic antibodies can be raised against first antibodies having specificity against the antigenic sites on the glycoprotein of the invention (i.e. the anti-idiotypic antibodies are anti-antibodies). Preferably monoclonal anti-idiotypic antibodies are used.

An assay for HTLV-III infection is important because the virus can be readily transferred from the peripheral blood leukocytes of antibody-positive people to leukocytes of antibody-negative people when the two are cultivated together. Popovic et al., Science, Vol. 219, 856–859 (1983). Consequently, it appears that there is great risk of infection involved in whole blood transfusions when the transfused blood contains infected cells. The assay is of importance because biological specimens from individuals exhibiting acquired immunodeficient syndrome (AIDS) give a positive test for antibodies to the antigenic determinant of the novel glycoprotein, thus facilitating diagnosis of that disease.

Consequently, the invention also embraces the method of assaying a biological specimen for the presence of antibody to HTLV-III-infected cells which comprises incubating said specimen with a polypeptide having an antigenic determinant or determinants immunologically cross-reactive with those of a first glycoprotein having a molecular weight of approximately 120,000 daltons (gp120), of which approximately 90,000 daltons is the unglycosylated moiety (p90), or with a second glycoprotein having a molecular weight of approximately 160,000 daltons (gp160) of which the 90,000 dalton unglycosylated moiety is substantially identical to the unglycosylated moiety of the first glycoprotein, which glycoproteins occur on the cell surface of cells infected with HTLV-III, and determining whether or not an immunocomplex is formed between said antibody and said polypeptide.

The invention also embraces a method of assaying a biological specimen for the presence of antigenic determinant or determinants immunologically cross-reactive with the determinants of the glycoproteins of molecular weight 120,000 daltons, or 160,000 daltons. The determinants to be assayed may occur on the stated glycoproteins themselves or on other polypeptides. They may be in free circulation in the body fluids or in lymphocytes. The assay can be carried out by known immunoassay methods, using antibodies, monoclonal or polyvalent, having immune reactivity with the antigenic determinants found on the stated glycoproteins. For example competitive immunoassays or immunometric (sandwich) assays can be used.

DESCRIPTION OF THE PREFERRED EMBODIMENTS

Figure 1:
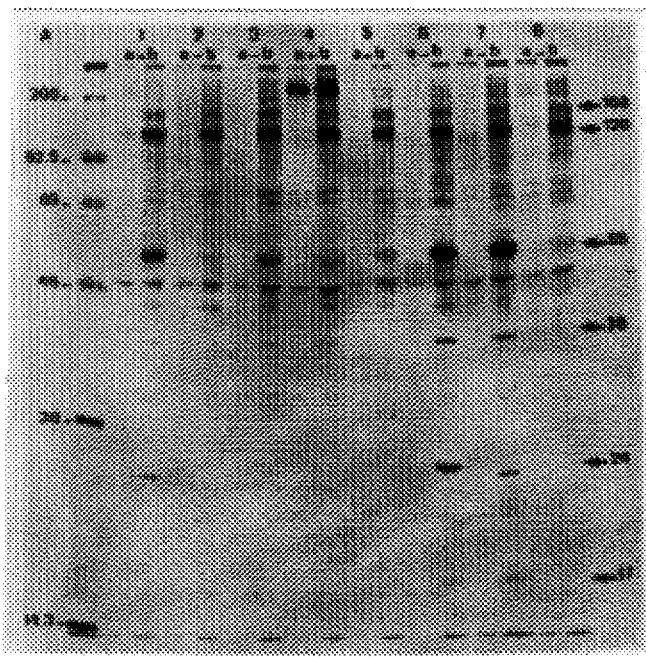
FIG. 1 represents an autoradiogram showing specific activities of gp120 and gp160 as determined by gel electrophoresis.

The glycoproteins of the present invention have a molecular weight of approximately 120,000 daltons and approximately 160,000 daltons as determined by sodium dodecyl sulfate (SDS) gel electrophoresis and are soluble in SDS buffer consisting of 0.15M sodium chloride, 0.05M Tris hydrochloride PH 7.2, 1% Triton X-100, 1% sodium deoxycholate, 0.1% sodium dodecylsulfate, and 1 mM phenylmethylsutfonyl fluoride. Triton X-100 is a nonionic detergent (octylphenoxy polyethoxy (9–10) ethanol). The unglycosylated moiety of the 120,000 dalton and of 160,000 dalton glycoprotein has a molecular weight of approximately 90,000 daltons and contains substantially the same antigenic determinant or determinants as do the glycoproteins themselves.

The glycoproteins can be obtained from HTLV-III-infected cells. A variety of cell lines have been prepared, which are permanently and persistently infected with HTLV-III; among them can be mentioned HTLV-III-infected H9 cells. Lymphadenopathy Associated Virus-(LAV) infected NC37 cells, and Molt 3 and HUT 78 cells infected with fresh AIDS virus isolates. It may be that the exact sizes of the novel glycoproteins are slightly different in different lines; however, the common immunologically cross-reactive portion of the glycoproteins is the same regardless of cell line, since it is a protein induced by HTLV-III. Thus, any cell which harbors the virus may be an appropriate source for the novel glycoproteins. In order to obtain the protein from any infected cells carrying the virus, the cells are metabolically labelled (e.g. with $^{35}$S-cysteine) and immunoprecipitated with antisera obtained from HTLV-III-infected subjects. The novel glycoproteins can then be detected and isolated by gel electrophoresis. By "HTLV" as used in the present specification and claims it is meant to include the virus generically. Thus any and all forms, subtypes, or variations of the virus are included.

For example, the glycoproteins are present at the cell surfaces of the HTLV-III-infected human T-cell line H9, LAV-infected NC37 cells, and Molt 3 and HUT 78 cells infected with fresh AIDS virus isolates. The glycoproteins can readily be separated from the cells of these cell lines by lysis thereof and SDS gel electrophoresis.

The purified and isolated glycoproteins or any antigen immunologically cross-reactive therewith can be employed as a standard antigen in any conventional assay procedure for detection in biological specimens of the presence of antibodies specific thereto, hence of the presence in the specimen of cells infected with HTLV-III and/or symptomatic of AIDS. The antibodies specific to such HTLV-III antigens are not found in patients suffering from diseases such as hepatitis which are not accompanied by HTLV-III infection.

The glycoproteins or polypeptides immunologically cross-reactive therewith can be labelled by conventional procedures with $^{125}$I or $^{35}$S or $^{3}$H for use in radioimmunoassay, with fluorescein for flourescent immunoassay, with enzyme for enzyme immunoassay or with biotin, for biotin-avidin linked assays. It can be employed labelled or unlabelled as desired, in competitive immunoassays, as well as in double antibody assays using two antibodies, either of the idiotype:antiidiotype variety or more particularly of the second antibody type using an anti-Fc antibody, or other assays.

Alternatively, the novel glycoproteins or polypeptides immunologically cross-reactive therewith could be immobilized on an insoluble phase, such as an insoluble resin, and detection of the anti-glycoprotein antibodies is carried out by measuring their binding to the insoluble phase. Insoluble phases also include latex particles, which when coated with the novel glycoprotein or its immunologically cross-reactive polypeptides and subjected to anti-glycoprotein antibody, will aggultinate. Yet other insoluble phases include test tubes, vials, titration wells, and the like, to which the novel glycoprotein or its immunologically cross-reative polypeptide can be bound, and antibody thereto detected by double antibody techniques or Protein-A dependent techniques.

The assay for antibodies which recognize HTLV-III-induced cell surface antigens may utilize the glycoprotein or glycoproteins or the unglycosylated moiety of MW 120,000 daltons, 160,000 daltons and 90,000 daltons respectively in crude form, and is not limited to using these proteins in substantially pure form. For example, the glycoprotein(s) may be first substantially purified and then mixed together. Alternatively cruder mixtures can also be used.

The elements necessary for carrying out the diagnostic methodology described hereinbefore may be present in a kit. Such kit comprises a carrier being compartmentalized to receive therein one or more containers, which of said containers comprising one or more elements necessary to carry out the tests.

For example, the first container may contain one or both of the purified glycoproteins or its immunologically cross-reactive polypeptides in detectably labelled or in insolubilized form.

A second container may comprise anti IgG antibody, polyclonal or monoclonal, useful in double antibody binding assay, or elements needed for detection of the label on the glycoprotein or its immunologically cross-reactive polypeptides (e.g. chromogenic substrates).

Additional containers may comprise varying amounts of one of the glycoproteins or its immunologically cross-reactive polypeptides which can be used to prepare a standard curve into which experimental results can be interpolated. The materials may be present in the kit by themselves, in solution, freeze-dried, or in admixture with other inert materials, such as inert proteins, and the like.

The biological specimens tested may include blood, serum, lymphocytes, urine, tissues, saliva, feces, and the like. Of particular interest is the screening of blood in blood banks, to assure that the blood is not contaminated with HTLV-III. Screening of blood-derived products, such as vaccines, can also be done by the methods of the invention.

The following specific examples are intended to illustrate more fully the nature of the invention without acting as a limitation upon its scope.

Characterization of Proteins

The reactivity of serum samples positive for antibodies to HTLV-III-induced cell membrane antigens (HTLV-III-MA) was determined by RIP-SDS-PAGE, the proteins being separated on a 12.5% SDS-polyacrylamide gel with 3.5% stacking gel using the Laemmli buffer system.

Uninfected H9 cells (a), and H9 cells infected with HTLV-III(b) at their peak log phase of growth were harvested and exposed to [$^{35}$S]-cysteine (100 µCi/ml; specific activity 957.5 Ci/mmole) for 14–16 hours. A soluble cell lysate was obtained and cleared once with a reference negative control serum bound to Protein A Sepharose CL4B (Protein A beads) as described by Essex et al., (1983) Science 220:859, before portions were reacted with 8 µl of the following sera preabsorbed with Protein A beads with the results shown in FIG. 1 of the drawing: (A) sera from 8 AIDS patients that were positive for anti-HTLV-III-MA (lanes 1–8), (B) sera from 4 ARC patients that were positive for anti-HTLV-III-MA (lanes 1–4) and sera from 4 healthy homosexuals that were positive for anti-HTLV-III-MA (lanes 5–8); (C) sera from 2 healthy homosexuals that were negative for anti-HTLV-III-MA (lanes 1–2), sera from 2 laboratory workers that were negative for anti-HTLV-III-MA (lanes 3–4), a mouse monoclonal antibody to p24 of HTLV-III (lane 5), a normal rabbit serum (lane 6), a reference rabbit antiserum to disrupted HTLV-III (lane 7), and a positive control ARC patient (lane 8). The molecular weight markers were $^{14}$C-labeled myosin (200,000), phosphorylase-b (92,500), bovine serum albumin (69,000), ovalbumin (46,000), carbonic anhydrase (30,000) and lysozyme (14,300).

Preparation of Labeled Glycoprotein

Figures 1, 2:
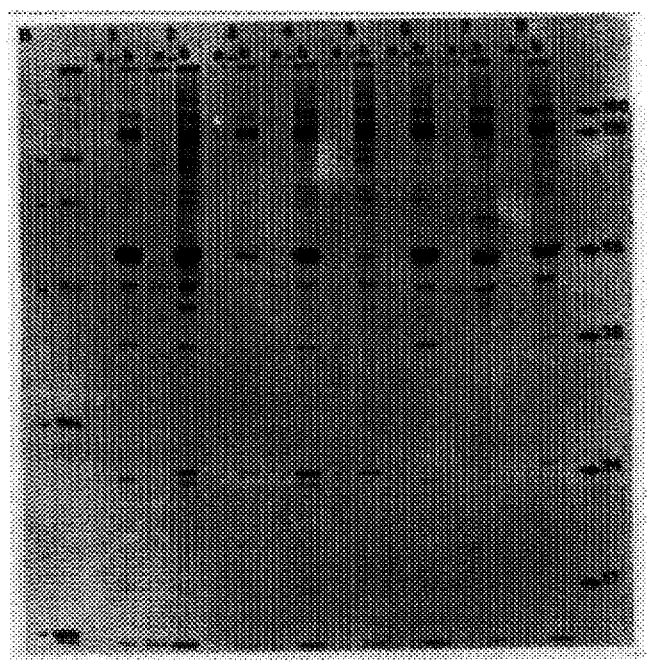
FIG. 2 represents an autoradiogram showing specific activities of gp120 and gp160 as determined by gel electrophoresis.

H9 cells infected with HTLV-III at their peak log phase of growth were harvested and exposed to [$^{35}$S]-cysteine (100 µCi/ml; specific activity 957.5 Ci/mmole) for 14–16 hours. To enrich glycoprotein fractions, the soluble cell lysate was first reacted with lentil lectin sepharose 4B at a ratio of 20×10⁶ cells to 1 ml of lentil lectin 4B at 4° C. for 3 hours. Deoxycholate-free RIPA buffer in the presence of 5% methyl αD mannoside was used to elute the glycoprotein fraction. The glycoprotein fraction was analyzed using RIP-SDS-PAGE with human sera positive for anti-HTLV-III-MA. The [$^{35}$S]-cysteine labeled glycoproteins were reacted with 8 μl of the following sera with the results shown in FIG. 2: 4 sera from 4 AIDS patients positive for anti-HTLV-III-MA (lanes 1–4), 2 sera from 2 ARC patients that were positive for anti-HTLV-III-MA (lanes 5–6), 2 sera from 2 healthy homosexuals that were positive for anti-HTLV-III-MA (lanes 7–8), 2 sera from healthy homosexuals that were negative for anti-HTLV-III-MA (lanes 9–10), and 2 sera from 2 laboratory workers that were negative for anti-HTLV-III-MA (lanes 11–12).

Preparation of Labelled Unglycosylated Moiety of Glycoprotein

Figures 1, 2, 3:
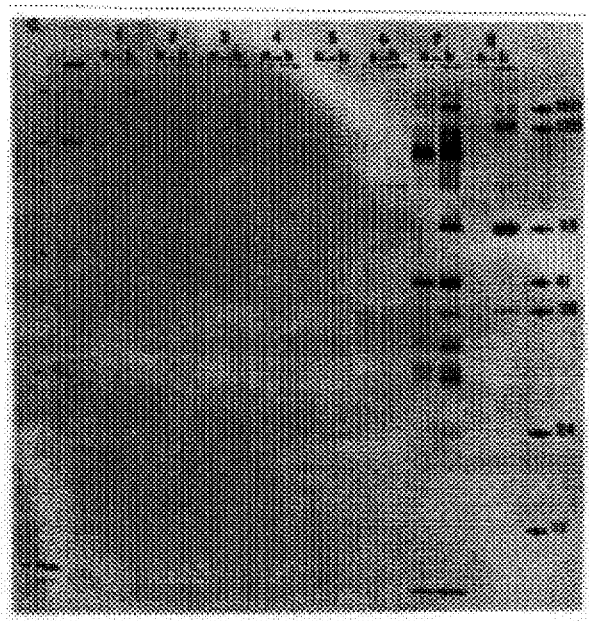
FIG. 3 represents an autoradiogram illustrating specific activity of p90 as determined by gel electrophoresis.
Figure 3:
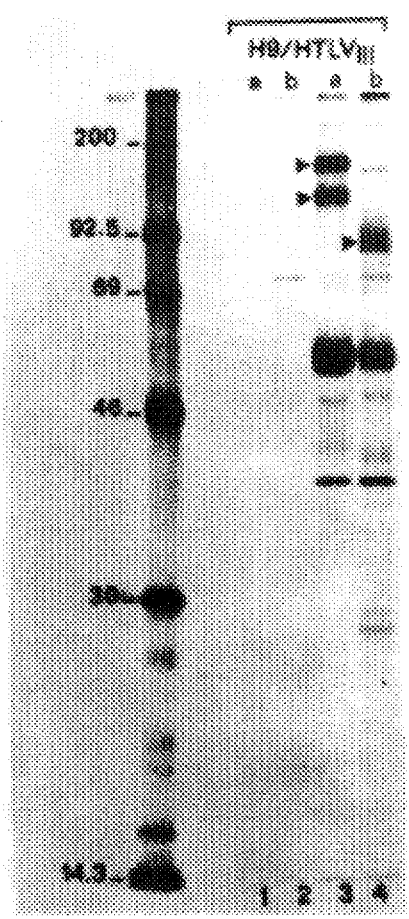
Figure 2:
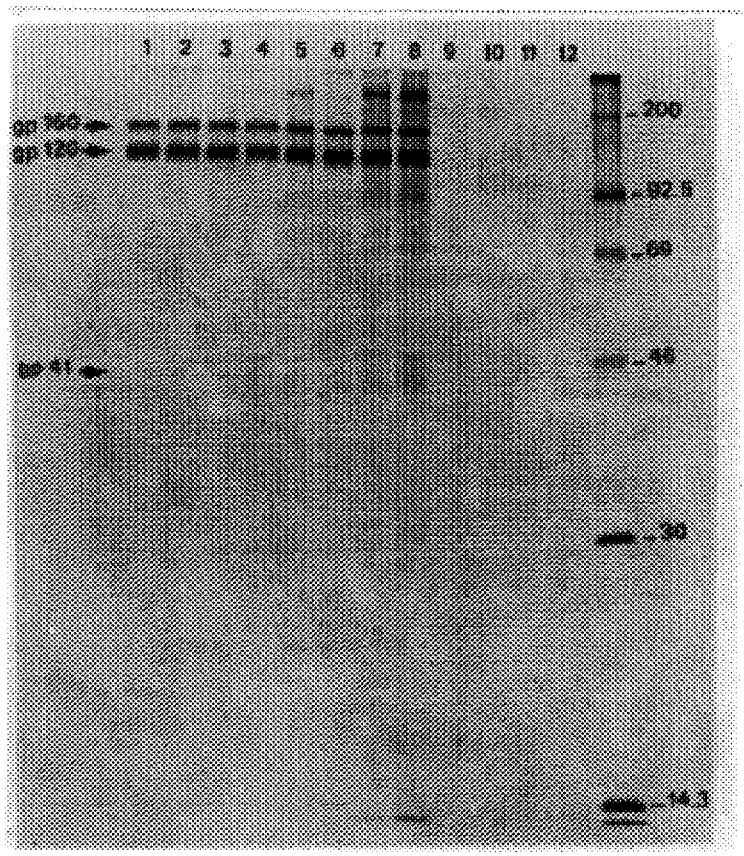

HTLV-III-infected H9 cells at their peak log phase of growth were harvested and resuspended in McCoy's 5A medium supplemented with 10% fetal bovine serum, 1% of antibiotic-antimycotic mixture, and 20 μg/ml of tunicamycin for 2 hours. After this trimming step, the cells were labelled with [$^{35}$S]-cysteine as described above in the presence of 20μg/ml of tunicamycin for 3 hours. The labelled material was then subjected to the same lysing and preclearing procedures as described above. The proteins from treated and untreated cells were analyzed by human sera positive for anti-HTLV-III-MA using RIP-SDS-PAGE as shown in FIG. 3, left hand lane. Soluble cell lysates from tunicamycin-untreated (a) and—treated cells (b) were reacted with: 8 μl of a reference serum negative for antibodies to HTLV-III (lanes 1–2 and 7–8) and 8 μl of a reference serum positive foe antibodies to HTLV-III (9) from an ARC patient (lanes 3–7), with the results shown in FIG. 3.

What is claimed is:

1. A method for assaying a biological specimen for the presence of antibody as an indicium of a patient's infection with HTLV-III, which comprises,
    a) incubating said specimen with a marker composition comprising an antigen selected from the group consisting of: 1) gp160; 2) gp120; 3) p90; and 4) polypeptides having an antigenic determinant in common with gp120 that is specifically immunoreactive with antibody that is specific for HTLV-III gp160, gp120, or p90, said antigen having a purity level in said marker composition higher than the purity level of said antigen (if any) in HTLV-III viral lysate; and
    b) determining whether an immunocomplex is formed between antibody in said specimen and said marker composition, indicative of infection with HTLV-III.

2. The method of claim 1 in which said polypeptide is gp160.

3. The method of claim 1 in which said polypeptide is gp120.

4. The method of claim 1 in which said polypeptide is p90.

5. A kit useful for assaying a biological specimen for the presence of antibody as an indicium of a patient's infection with HTLV-III, said kit being compartmentalized to receive in close confinement therein one or more containers, said kit comprising:
    a) a first container containing a marker composition comprising an antigen selected from the group consisting of: 1) gp160; 2) gp120; 3) p90; and 4) polypeptides having an antigenic determinant in common with gp120 that is specifically immunoreactive with antibody that is specific for HTLV-III gp160, gp120, or p90, said antigen having a purity level in said marker composition higher than the purity level of said antigen (if any) in HTLV-III viral lysate; and
    b) a second container containing means for detecting the formation of an immunocomplex between antibody in said specimen and said marker composition, indicative of infection with HTLV-III.

6. The kit of claim 5 in which said polypeptide is gp160.

7. The kit of claim 5 in which said polypeptide is gp120.

8. The kit of claim 5 in which said polypeptide is p90.

9. A method for assaying a biological specimen for the presence of antibody directed against HTLV-III as an indicium of a patient's infection with HTLV-III, which comprises,
    a) incubating said specimen with a marker composition comprising an antigen selected from the group consisting of: 1) gp160; 2) gp120; 3) p90; and 4) polypeptides having an antigenic determinant in common with gp120 that is specifically immunoreactive with antibody that is specific for HTLV-III gp160, gp120, or p90, said antigen being at least as pure in said marker composition as it is when obtained by affinity chromatography; and
    b) determining whether an immunocomplex is formed between said marker composition and said specimen indicative of infection with HTLV-III.

10. A kit useful for assaying a biological specimen for the presence of antibody as an indicium of a patient's infection with HTLV-III, said kit being compartmentalized to receive in close confinement therein one or more containers, said kit comprising:
    a) a first container containing a marker composition comprising an antigen selected from the group consisting of: 1) gp160; 2) gp120; 3) p90; and 4) polypeptides having an antigenic determinant in common with gp120 that is specifically immunoreactive with antibody that is specific for HTLV-III gp160, gp120, or p90, said antigen being at least as pure in said marker composition as it is when obtained by affinity chromatography; and
    b) a second container containing means for detecting the formation of an immunocomplex between said antibody and said marker composition, indicative of infection with HTLV-III.

* * * * *